(12) United States Patent
Fu

(10) Patent No.: US 7,041,671 B2
(45) Date of Patent: May 9, 2006

(54) PYRROLO[1,2-B]PYRIDAZINE COMPOUNDS AND THEIR USES

(75) Inventor: Jian-min Fu, Burnaby (CA)

(73) Assignee: Pfizer Inc, New York, NY (US)

( * ) Notice: Subject to any disclaimer, the term of this patent is extended or adjusted under 35 U.S.C. 154(b) by 153 days.

(21) Appl. No.: 10/799,406

(22) Filed: Mar. 12, 2004

(65) Prior Publication Data

US 2004/0204414 A1    Oct. 14, 2004

Related U.S. Application Data

(60) Provisional application No. 60/459,744, filed on Apr. 2, 2003.

(51) Int. Cl.
| C07D 487/04 | (2006.01) |
| A61K 31/5025 | (2006.01) |
| A61P 25/22 | (2006.01) |
| A61P 25/24 | (2006.01) |

(52) U.S. Cl. .................................. 514/248; 544/235

(58) Field of Classification Search ................ 544/235; 514/248

See application file for complete search history.

(56) References Cited

FOREIGN PATENT DOCUMENTS

| EP | 1085021 | 5/1999 |
| WO | 9808847 | 3/1998 |
| WO | 02072101 | 9/2002 |
| WO | 02072202 | 9/2002 |

OTHER PUBLICATIONS

Chorvat et al. (J. Med. Chem. (2000), 42: 833-848).*
(He et al. J. Med. Chem. (2000), 43:449-456).*

* cited by examiner

*Primary Examiner*—Kahsay Habte
(74) *Attorney, Agent, or Firm*—Steve T. Zelson; Jolene W. Appleman

(57) ABSTRACT

Disclosed are novel CRF receptor antagonists and their use as treatment of a variety of disorders, including disorders manifesting hypersecretion of CRF or associated with CRF or CRF receptors, such as anxiety, and depression. CRF receptor antagonists of the invention have the structure of formula (I):

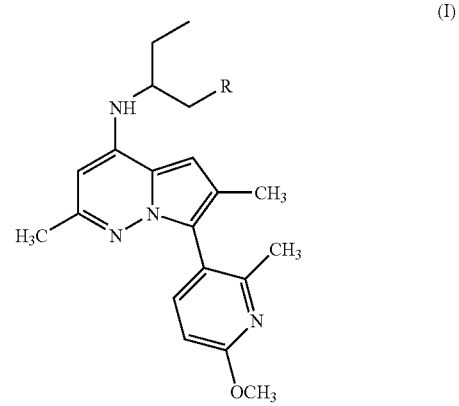

including stereoisomers or mixture of stereoisomers, pharmaceutically acceptable prodrugs, or pharmaceutically acceptable salts thereof, wherein in formula (I) R is H or Me.

4 Claims, No Drawings

PYRROLO[1,2-B]PYRIDAZINE COMPOUNDS AND THEIR USES

This application claims the benefit of U.S. Provisional Application No. 60/459,744, filed Apr. 2, 2003.

FIELD OF THE INVENTION

The present invention relates generally to compounds that bind to CRF receptors, and particularly to substituted pyrrolo[1,2-b]pyridazine derivatives as CRF, receptor antagonists and use thereof as a treatment for disorders that are associated with CRF or CRF, receptors.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, CRF is known to have a broad extrahypothalmic distribution in the CNS, contributing therein to a wide spectrum of autonomic behavioral and physiological effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is evidence that CRF plays a significant role in integrating the response in the immune system to physiological, psychological, and immunological stressors, in psychiatric disorders and neurological diseases including depression, anxiety-related disorders and feeding disorders, and in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [J. E. Blalock, *Physiological Reviews* 69:1 (1989); J. E. Morley, *Life Sci.* 41:527 (1987); E. B. De Souze, *Hosp. Practice* 23:59 (1988)].

CRF has been implicated in the etiology of mood disorder, also known as affective disorder. It was shown that in individuals afflicted with affective disorder, or major depression, the concentration of CRF in the cerebral spinal fluid (CSF) is significantly increased. [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders. Anxiety disorders are a group of diseases, recognized in the art, that includes phobic disorders, anxiety states, post-traumatic stress disorder and a typical anxiety disorders [The Merck Manual of Diagnosis and Therapy, 16$^{th}$ edition (1992)]. Emotional stress is often a precipitating factor in anxiety disorders, and such disorders generally respond to medications that lower response to stress. Excessive levels of CRF are known to produce anxiogenic effects in animal models [see, e.g., Britton et al., 1982; Berridge and Dunn, 1986 and 1987]. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn, *Regul. Peptides* 16:83 (1986)]. Studies using the putative CRF receptor antagonist α-helical ovine CRF (9–41) in a variety of behavioral paradigms demonstrates that the antagonist produces "anxiolytic-like" effects that are qualitatively similar to the benzodiazepines [C. W. Berridge and A. J. Dunn, *Horm. Behav.* 21:393 (1987), *Brain Research Reviews* 15:71 (1990); G. F. Koob and K. T. Britton, In: *Corticotropin-Releasing Factor: Basic and Clinical Studies of a Neuropeptide*, E. B. De Souza and C. B. Nemeroff eds., CRC Press p. 221 (1990)]. Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist Ro 15–1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)]. The use of $CRF_1$ antagonists for the treatment of Syndrome X has also been described in U.S. patent application Ser. No. 09/696,822, filed Oct. 26, 2000, and European Patent Application No. 003094414, filed Oct. 26, 2000. Methods for using $CRF_1$ antagonists to treat congestive heart failure are described in U.S. Ser. No. 09/248,073, filed Feb. 10, 1999, now U.S. Pat. No. 6,043,260 (Mar. 28, 2000).

It has also been suggested that $CRF_1$ antagonists are useful for treating arthritis and inflammation disorders [Webster EL, et al., *J Rheumatol* 29(6):1252 (2002); Murphy EP, et al., *Arthritis Rheum* 44(4):782 (2001)]; stress-related gastrointestinal disorders [Gabry, K. E.et al., *Molecular Psychiatry* 7(5): 474 (2002),]; and skin disorders [Zouboulis, C. C.et al., *Proc. Natl. Acad. Sci.* 99: 7148 (2002)].

It was disclosed recently that, in an animal model, stress-induced exacerbation of chronic contact dermatitis is blocked by a selective $CRFR_1$ antagonist, suggesting that $CRFR_1$ is involved in the stress-induced exacerbation of chronic contact dermatitis and that $CRFR_1$ antagonist may be useful for treating this disorder. [Kaneko K, Kawana S, Arai K, Shibasaki T. *Exp Dermatol* 12(1): 47 (2003)].

EP1085021 discloses pyrrolo[1,2-b]pyridazine compounds as sPLA2 inhibitors. The following publications each describes $CRF_1$ antagonist compounds; however, none disclose the specific compounds provided herein: WO 98/08847 (International Publication Date 5 Mar. 1998); WO 02/072101 (International Publication Date 19 Sep. 2002);

WO 02/072202 (International Publication Date 19 Sep. 2002). The present invention is a selection invention from WO 98/08847.

It is an object of the invention to provide novel pyrrolo[1,2-b]pyridazine derivatives, which are $CRF_1$ receptor antagonists.

It is another object of the invention to provide novel compounds as treatment of disorders or conditions that are associated with CRF or $CRF_1$ receptors, such as anxiety disorders, depression, and stress related disorders.

It is another object of the invention to provide a method of treating disorders or conditions that are associated with CRF or $CRF_1$ receptors, such as anxiety disorders, depression, and stress related disorders.

It is yet another object of the invention to provide a pharmaceutical composition useful for treating disorders or conditions that are associated with CRF or $CRF_1$ receptors, such as anxiety disorders, depression, and stress related disorders.

There are other objects of the invention which will be evident or apparent from the description of the invention in the specification of the application.

SUMMARY OF THE INVENTION

In one aspect, the present invention provides a compound of formula (I), or a stereoisomer, a pharmaceutically acceptable salt, or a prodrug thereof, which is potent antagonist of $CRF_1$ receptor.

In another aspect, the present invention provides a compound of formula (I), or a stereoisomer, a pharmaceutically acceptable salt, or a prodrug thereof, which is useful for the treatment of a disorder in a warm-blooded animal, which disorder manifests hypersecretion of CRF, or the treatment of which disorder can be effected or facilitated by antagonizing $CRF_1$ receptors. Examples of such disorders include anxiety-related disorders such as anxiety states, generalized anxiety disorder, phobic disorders, social anxiety disorder, anxiety with co-morbid depressive illness, panic disorder, obsessive-compulsive disorder, post-traumatic stress disorder, and a typical anxiety disorders; mood disorders such as depression, including major depression, single episode depression, recurrent depression, child abuse induced depression, and postpartum depression; dysthemia; bipolar disorders; and cyclothymia; supranuclear palsy; immune suppression; inflammatory disorders such as rheumatoid arthritis and osteoarthritis; fertility problems including infertility; pain; asthma; allergies; sleep disorders induced by stress; pain perception such as fibromyalgia; fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; head traumas; spinal cord trauma; ischemic neuronal damage such as cerebral hippocampal ischemia; excitotoxic neuronal damage; epilepsy; cardiovascular and heart related disorders such as hypertension, tachycardia, congestive heart failure, and stroke; immune dysfunctions including stress induced immune dysfunctions such stress induced fevers, porcine stress syndrome, bovine shipping fever, equine paroxysmal fibrillation, and dysfunctions induced by confinement in chickens, sheering stress in sheep or human-animal interaction related stress in dogs; muscular spasms; urinary incontinence; senile dementia of the Alzheimer's type; multiinfarct dementia; amyotrophic lateral sclerosis; chemical dependencies and addictions such as dependences on alcohol, cocaine, heroin, benzodiazepines, or other drugs; osteoporosis; psychosocial dwarfism, hypoglycemia, and skin disorders such as acne, psoriasis, chronic contact dermatitis, and stress-exacerbated skin disorders. They are also useful for promoting smoking cessation and hair growth, or treating hair loss.

In still another aspect, the present invention provides for the use of a compound of formula (I), and stereoisomers, pharmaceutically acceptable salts, and prodrugs thereof, for treatment of a disorder disclosed herein above.

In still another aspect, the present invention provides for a composition comprising a compound of formula (I), and stereoisomers, pharmaceutically acceptable salts, and prodrugs thereof, useful for treatment of a disorder disclosed herein above.

In still another aspect, the present invention provides for the use of a compound of the invention in a binding assay, wherein one or more of the compounds may be joined to a label, where the label can directly or indirectly provide a detectable signal. Various labels include radioisotopes, fluorescers, chemiluminescers, specific binding molecules, particles, e.g. magnetic particles, and the like.

In yet another aspect, the present invention relates to the use of the compounds of the invention (particularly labeled compounds of this invention) as probes for the localization of receptors in cells and tissues and as standards and reagents for use in determining the receptor-binding characteristics of test compounds.

Labeled compounds of the invention may be used for in vitro studies such as autoradiography of tissue sections or for in vivo methods, e.g. PET or SPECT scanning. Particularly, compounds of the invention are useful as standards and reagents in determining the ability of a potential pharmaceutical to bind to the $CRF_1$ receptor.

DETAILED DESCRIPTION OF THE INVENTION

In a first aspect the present invention provides a compound of formula (I)

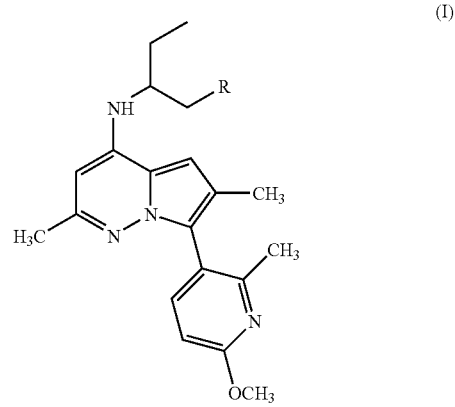

(I)

or a stereoisomeric form thereof, a mixture of stereoisomeric forms thereof, a pharmaceutically acceptable salt thereof, or a prodrug thereof, wherein in formula (I) R is H or Me.

Compounds provided herein can have one or more asymmetric centers or planes, and all chiral (enantiomeric and diastereomeric) and racemic forms of the compound are included in the present invention. Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by an asymmetric synthesis route enabling the preparation of enantiomerically enriched material. The present invention encompasses all possible tautomers of the compounds represented by formula (I).

Compounds of the invention can generally be prepared using the synthetic routes illustrated in Scheme 1 indicated below. Starting materials are either commercially available or can be prepared by procedures known in the art.

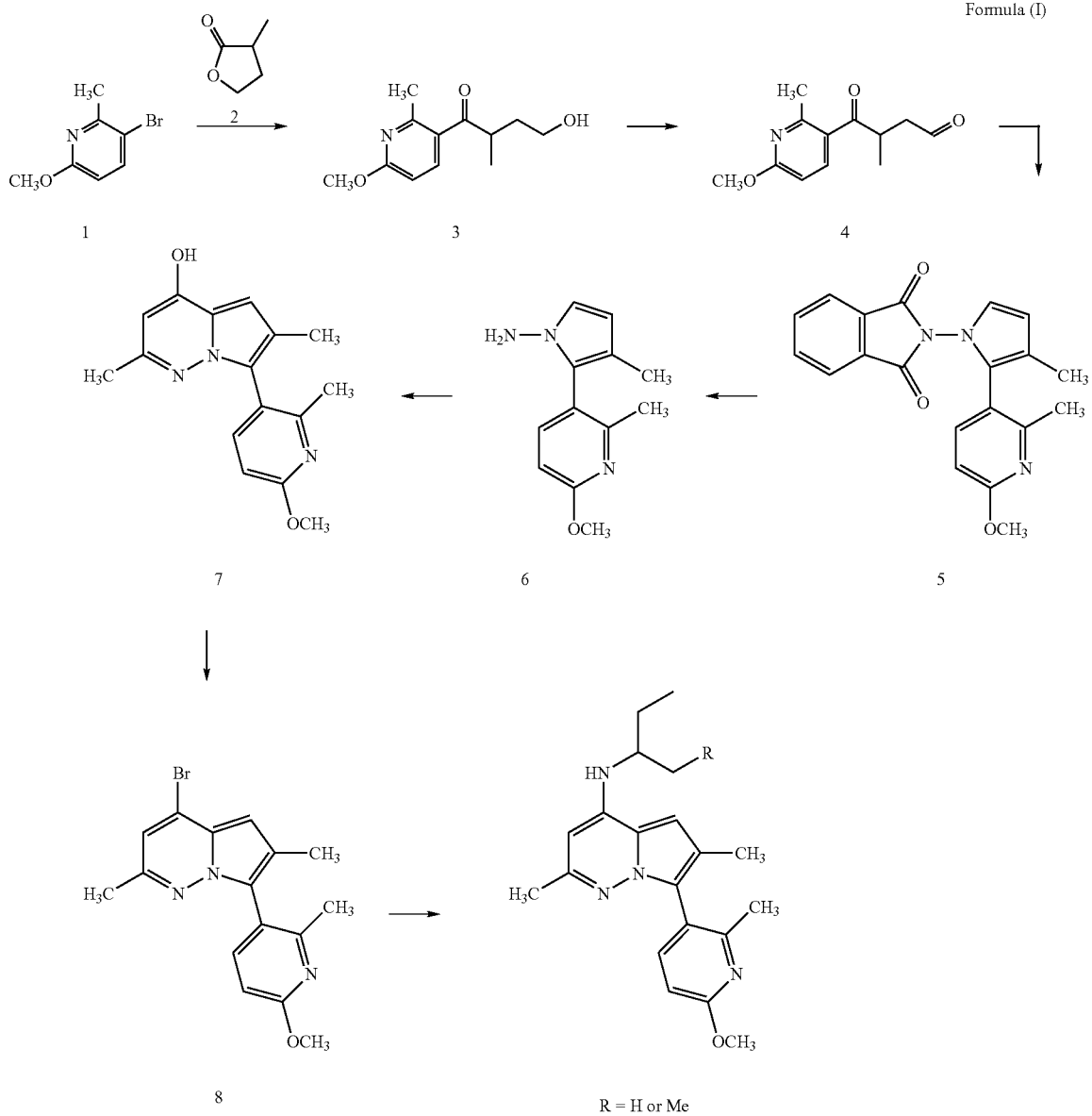

Scheme 1

Formula (I)

R = H or Me

2-Methyl-3-bromo-6-methoxypyridine (1) can be treated with a strong base such as n-butyllithium or t-butyllithium and react with α-methyl-γ-butyrolactone (2) to form ketone 3. Oxidation of alcohol 3 to aldehyde 4 can be accomplished by a method such as but not limited to Swern oxidation. The generated dicarbonyl compound 4 can react with N-aminophthalimide to provide the substituted pyrrole compound 5. Treatment of 5 with hydrazine thus produces the 1-aminopyrrole compound 6, which can react with a β-ketoester or ethyl trans-3-ethoxycrotonate in solvent such as but not limited to chloroform, toluene or tetrahydrofuran in the presence of catalytic amount of acid such as p-toluenesulfonic acid in a reaction vessel equipped with a Dean-Stark apparatus with molecular sieves to provide the bicyclic compound 7. The hydroxyl group in compound 7 can be converted into a bromo group by reacting with phosphorus tribromide in refluxing bromobenzene. The generated bromo compound 8 can undergo palladium (e.g. Pd(OAc)$_2$, Pd$_2$(dba)$_3$, etc) catalyzed amination reaction (see, Wolfe, J. P. and Buchwald, S. L. *J. Org. Chem.* 2000, 65, 1144) with 1-ethylpropylamine or 2-butylamine to form the compound of formula (I).

The present invention also encompasses pharmaceutically acceptable salts of the compounds of formula (I). Pharmaceutically acceptable salts of the invention can be prepared from suitable inorganic acids or organic acids. The nature of the salt is not critical, provided that it is pharmaceutically acceptable. Suitable pharmaceutically-acceptable salts of compounds of formula I may be prepared from inorganic acid or from organic acid. Examples of such inorganic acids are hydrochloric, hydrobromic, hydroiodic, nitric, carbonic, sulfuric and phosphoric acid. Examples of such organic acids include aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Lists of suitable salts are found in Remington's Pharmaceutical Sciences, 17th ed., Mack Publishing Company, Easton, Pa., 1985, p. 1418, the disclosure of which is hereby incorporated by reference. Pharmaceutically acceptable salts of the compounds of the invention can be prepared by conventional chemical methods. Generally, such salts can be prepared by reacting the free base forms of the compounds with a stoichiometric amount of the appropriate acid in water or in an organic solvent, or in a mixture of the two; generally, non-aqueous media like ether, ethyl acetate, ethanol, isopropanol, or acetonitrile are preferred.

In another aspect, the present invention provides a prodrug of a compound of formula (I). The prodrug is prepared with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). See e.g. T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs of the invention can be readily prepared from the compounds of formula (I) using methods known in the art. See, e.g. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172–178, 949–982 (1995). For example, prodrugs of the compounds of formula (I) can be prepared by modifying amine group on the compound in such a way that the modifications are cleaved, either in routine manipulation or in vivo, to the parent compound. Examples of forms of the prodrugs prepared in such a way include biohydrolyzable amides, biohydrolyzable carbamates, and thiocarbamates.

In another aspect the invention provides isotopically-labeled compounds, which are identical to the compounds of formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, and chlorine, such as $^3$H, $^{11}$C, and $^{14}$C. Compounds of formula (I) that contain the aforementioned isotopes and/or other isotopes of other atoms are within the scope of the invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly useful in PET (positron emission tomography). Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances. Isotopically labeled compounds of formula (I) of this invention can generally be prepared by carrying out the synthetic procedures by substituting an isotopically labeled reagent for a non-isotopically labeled reagent.

The compounds of formula (I) are antagonists at the CRF, receptor, capable of inhibiting the specific binding of CRF to CRF1 receptor and antagonizing activities associated with CRF. The effectiveness of a compound as a CRF receptor antagonist may be determined by various assay methods. A compound of formula (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). CRF receptor affinity may be determined by binding studies that measure the ability of a compound to inhibit the binding of a radiolabeled CRF (e.g., [125 I]tyrosine-CFR) to its receptor (e.g., receptors prepared from rat cerebral cortex membranes). The radioligand binding assay described by DeSouza et al. (supra 1987) provides an assay for determining a compound's affinity for the CRF receptor. Such activity is typically calculated from the IC$_{50}$ as the concentration of a compound necessary to displace 50% of the radiolabeled ligand from the receptor, and is reported as a "Ki" value calculated by the following equation:

$$Ki = \frac{IC_{50}}{1 + L/K_D}$$

where L=radioligand and K$_D$=affinity of radioligand for receptor (Cheng and Prusoff *Biochem. Pharmacol.* 22:3099, 1973). An example of the receptor binding assay is provided in Example A below.

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra 1987) provides an assay for determining a compound's ability to antagonize CRF activity. Accordingly, CRF receptor antagonist activity may be determined by assay techniques which generally include an initial binding assay (such as disclosed by DeSouza (supra 1987)) followed by a cAMP screening protocol (such as disclosed by Battaglia (supra 1987)). An example of the CRF-stimulated adenylate cyclase activity assay is provided in Example C below.

Thus, in another aspect, the present invention provides a method of antagonizing $CRF_1$ receptors in a warm-blooded animal, comprising administering to the animal a compound of the invention at amount effective to antagonize $CRF_1$ receptors. The warm-blooded animal is preferably a mammal, and more preferably a human.

In another aspect, the present invention provides a method for screening for ligands for $CRF_1$ receptors, which method comprises: a) carrying out a competitive binding assay with $CRF_1$ receptors, a compound of formula (I) which is labeled with a detectable label, and a candidate ligand; and b) determining the ability of said candidate ligand to displace said labeled compound.

In another aspect, the present invention provides a method for detecting CRF receptors in tissue comprising: a) contacting a compound of formula (I), which is labeled with a detectable label, with a tissue, under conditions that permit binding of the compound to the tissue; and b) detecting the labeled compound bound to the tissue. Assay procedure for detecting receptors in tissues is well known in the art.

In another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the $CRF_1$ receptor. An example of the cell line that expresses the $CRF_1$ receptor and can be used in the in vitro assay is IMR32 cells known in the art.

Compounds of formula (I), or a stereoisomer, a pharmaceutically acceptable salt, or a prodrug thereof, are useful for the treatment of a disorder in a warm-blooded animal, which disorder manifests hypersecretion of CRF, or the treatment of which disorder can be effected or facilitated by antagonizing $CRF_1$ receptors. Examples of such disorders are described herein above.

Thus, in still another aspect, the present invention provides a method of treating a disorder described herein above, comprising administering to a warm-blooded animal a therapeutically effective amount of a compound of the invention. The warm-blooded animal is preferably a mammal, particularly a human.

Particular disorders that can be treated by the method of the invention preferably include anxiety-related disorders such as anxiety states, generalized anxiety disorder, phobic disorders, social anxiety disorder, anxiety with co-morbid depressive illness, panic disorder, obsessive-compulsive disorder, post-traumatic stress disorder, and a typical anxiety disorders; mood disorders such as dysthemia, bipolar disorders, cyclothymia, and depression including major depression, single episode depression, recurrent depression, child abuse induced depression, and postpartum depression; chemical dependencies and addictions such as dependences on alcohol, cocaine, heroin, benzodiazepines, or other drugs; inflammatory disorders such as rheumatoid arthritis and osteoarthritis; gastrointestinal diseases such as ulcers, irritable bowel syndrome, Crohn's disease, spastic colon, diarrhea, and post operative ilius and colonic hypersensitivity associated by psychopathological disturbances or stress; and skin disorders such as acne, psoriasis, chronic contact dermatitis, and stress-exacerbated skin disorders.

Particular disorders that can be treated by the method of the invention more preferably include anxiety-related disorders such as anxiety states, generalized anxiety disorder, phobic disorders, social anxiety disorder, anxiety with co-morbid depressive illness, panic disorder, obsessive-compulsive disorder, post-traumatic stress disorder, and a typical anxiety disorders and mood disorders such as dysthemia, bipolar disorders, cyclothymia, and depression including major depression, single episode depression, recurrent depression, child abuse induced depression, and postpartum depression.

Particular disorders that can be treated by the method of the invention even more preferably include generalized anxiety disorder and major depression The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

A compound of this invention can be administered to treat the above disorders by means that produce contact of the active agent with the agent's site of action in the body of a mammal, such as by oral, topical, dermal, parenteral, or rectal administration, or by inhalation or spray using appripropriate dosage forms. The term "parenteral" as used herein includes subcutaneous injections, intravenous, intramuscular, intrasternal injection or infusion techniques. The compound can be administered alone, but will generally be administered with a pharmaceutically acceptable carrier, diluent, or excipient.

Thus, in another aspect, the present invention provides a pharmaceutical composition comprising a compound of formula (I), a stereoisomer thereof, a pharmaceutically acceptable salt thereof, or a prodrug thereof, or a pharmaceutically acceptable salt of the prodrug thereof. In one embodiment, the pharmaceutical composition further comprises a pharmaceutically acceptable carrier, diluent, or excipient therefore. A "pharmaceutically acceptable carrier, diluent, or excipient" is a medium generally accepted in the art for the delivery of biologically active agents to warm-blooded animals, including humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa., 1985, the contents of which are incorporated herein by reference.

Compositions intended for oral use may be in the form of tablets, troches, lozenges, aqueous or oily suspensions, dispersible powders or granules, emulsion, hard or soft capsules, or syrups or elixirs, and can be prepared according to methods known to the art. Such compositions may contain one or more agents selected from the group consisting of sweetening agents, flavoring agents, coloring agents and preserving agents in order to provide pharmaceutically elegant and palatable preparations.

Tablets contain the active ingredient in admixture with pharmaceutically acceptable excipients, which are suitable for the manufacture of tablets. These excipients may be inert diluents such as calcium carbonate, sodium carbonate, lactose, calcium phosphate or sodium phosphate; granulating and disintegrating agents such as corn starch, or alginic acid; binding agents such as starch, gelatin or acacia, and lubricating agents such as magnesium stearate, stearic acid or talc. The tablets may be uncoated or they may be coated by known techniques to delay disintegration and absorption in the gastrointestinal tract and a delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long aliphatic alcohols, for example heptadecaethyleneoxycetanol, or condensation products of ethylene oxide with partial esters derived from fatty acids and a hexital such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

Suppositories for rectal administration of a compound of the invention can be prepared by mixing the compound with a suitable non-irritating excipient, which is solid at ordinary temperatures but liquid at the rectal temperature and will therefore melt in the rectum to release the drug. Examples of such materials are cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable solution or suspension may be formulated in a non-toxic parentally acceptable diluent or solvent, for example as a solution in 1,3-butanediol. Among the acceptable vehicles and solvents that may be employed are water, Ringers's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms suitable for administration generally contain from about 1 mg to about 100 mg of active ingredient per unit. In these pharmaceutical compositions, the active ingredient will ordinarily be present in an amount of about 0.5 to 95% by weight based on the total weight of the composition. Examples of dosage forms for administration of the compounds of this invention includes the following: (1) Capsules. A large number of units capsules are prepared by filling standard two-piece hard gelatin capsules each with 100 mg of powdered active ingredient, 150 mg lactose, 50 mg cellulose, and 6 mg magnesium stearate; (2) Soft Gelatin Capsules. A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried; (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

In another aspect, the present invention provides an article of manufacture comprising: a) a packaging material; b) a pharmaceutical agent comprising a compound of the invention contained within said packaging material; and c) a label or package insert which indicates that said pharmaceutical agent can be used for treating a disorder described below.

DEFINITIONS

The following definitions are used throughout the application, unless otherwise described.

The term "pharmaceutically acceptable" refer to those compounds, materials, compositions, and/or dosage forms which are, within the scope of sound medical judgment, suitable for use in contact with the tissues of or animals including humans without excessive toxicity, irritation, allergic response, or other problems or complications, commensurate with a reasonable benefit/risk ratio.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The term "racemate" or "racemic mixture" refers to a mixture of equal parts of enantiomers.

The term "prodrug" means a compound, other than a compound of formula (I), which is transformed in vivo to yield a compound of formula (I). The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "therapeutically effective amount," "effective amount," "therapeutic amount," or "effective dose" is meant that amount sufficient to elicit the desired pharmacological or therapeutic effects, thus resulting in effective prevention or treatment of the disease or condition.

The phrases "a compound of the invention," "a compound of the present invention," "compounds of the present invention," or "a compound in accordance with formula (I)" and the like, for brevity refer to compounds of formula (I), or stereoisomers thereof, pharmaceutically acceptable salts thereof, or prodrugs thereof, or pharmaceutically acceptable salts of a prodrug of compounds of formula (I).

The terms "treatment," "treat," "treating," and the like, are meant to include both slowing or reversing the progression of a disorder, as well as curing the disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

EXAMPLES

Without further elaboration, it is believed that one skilled in the art can, using the preceding description, practice the present invention to its fullest extent. Examples A–D illustrate various biological assays that can be used for determining the biological properties of the compounds of the inventions. These examples are provided to describe the invention in further detail. They are intended to illustrate and not to limit the invention in any way whatsoever. Those skilled in the art will promptly recognize appropriate variations from the procedures described in the examples.

Example A

In Vitro $CRF_1$ Receptor Binding Assay for the Evaluation of Biological Activity The following is a description of a standard in vitro binding assay for the evaluation of biological activity of a test compound on $CRF_1$ receptors. It is based on a modified protocol described by De Souza (De Souza, 1987).

The binding assay utilizes brain membranes, commonly from rats. To prepare brain membranes for binding assays, rat frontal cortex is homogenized in 10 mL of ice cold tissue buffer (50 mM HEPES buffer pH 7.0, containing 10 mM $MgCl_2$, 2 mM EGTA, 1 µg/mL aprotinin, 1 µg/mL leupeptin and 1 µg/mL pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 µg/mL.

Binding assays are performed in 96 well plates at a final volume of 300 µL. The assays are initiated by the addition of 150 µL membrane suspension to 150 µL of assay buffer containing $^{125}$I-ovine-CRF (final concentration 150 µM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvestor. Filters are washed three times with ice cold phosphate buffered saline pH 7.0 containing 0.01% Triton X-100. Filters are assessed for radioactivity in a Packard TopCount.

Alternatively, tissues and cells that naturally express CRF receptors, such as IMR-32 human neuroblastoma cells (ATCC; Hogg et al., 1996), can be employed in binding assays analogous to those described above.

A compound is considered to be active if it has a Ki value of less than about 10 µM for the inhibition of CRF.

Example B

Ex vivo $CRF_1$ Receptor Binding Assay for the Evaluation of Biological Activity The following is a description of a typical ex vivo $CRF_1$ receptor binding assay for assessing the biological activity of a test compound on $CRF_1$ receptors.

Fasted, male, Harlen-bred, Sprague-Dawley rats (170–210 g) were orally dosed with test compound or vehicle, via gastric lavage between 12:30 and 2:00 PM. Compounds were prepared in vehicle (usually 10% soybean oil, 5% polysorbate 80, in dH20). Two hours after drug administration, rats were sacrificed by decapitation, frontal cortices were quickly dissected and placed on dry ice, then frozen at −80° C. until assayed; trunk blood was collected in heparinized tubes, plasma separated by centrifugation (2500 RPM's for 20 minutes), and frozen at −20° C.

On the day of the binding assay, tissue samples were weighed and allowed to thaw in ice cold 50 mM Hepes buffer (containing 10 mM $MgCl_2$, 2 mM EGTA, 1 µg/mL aprotinin, 1 µg/mL leupeptin hemisulfate, and 1 µg/mL pepstatin A, 0.15 mM bacitracin, and 0.1% ovalbumin, pH=7.0 at 23° C.) and then homogenized for 30 sec at setting 5 (Polytron by Kinematica). Homogenates were incubated (two hours, 23° C., in the dark) with [$^{125}$I] CRF (0.15 nM, NEN) in the presence of assay buffer (as described above) or DMP-904 (10 μM). The assay was terminated by filtration (Packard FilterMate, GF/C filter plates); plates were counted in Packard TopCount LSC; total and non-specific fmoles calculated from DPM's. Data are expressed as % of vehicle controls (specific fmoles bound). Statistical significance was determined using student's t-test.

Example C

Inhibition of CRF Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Example D

In Vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). A compound may be tested in any species of rodent or small mammal.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I)

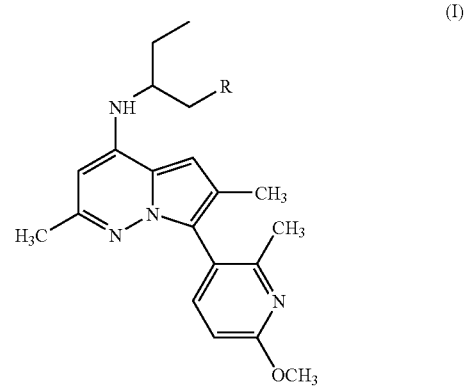

or a stereoisomeric form thereof, or a mixture of stereoisomeric forms thereof, or a pharmaceutically acceptable salt thereof, wherein in formula (I) R is H or Me.

2. A compound according to claim 1, which is N-(1-ethylpropyl)-7-(6-methoxy-2-methylpyridin-3-yl)-2,6-dimethylpyrrolo[1,2-b]pyridazin-4-amine.

3. A compound according to claim 1, which is 7-(6-methoxy-2-methylpyridin-3-yl)-2,6-dimethyl-N-[(1S)-1-methylpropyl]pyrrolo[1,2-b]pyridazin-4-amine.

4. A pharmaceutical composition comprising a compound of any one of claims 1 to 3, and a pharmaceutically acceptable carrier.

* * * * *